United States Patent [19]

Miller

[11] Patent Number: 5,009,969

[45] Date of Patent: Apr. 23, 1991

[54] DUAL ACTION SUNSCREEN COMPOSITION

[75] Inventor: Gary A. Miller, Monroe, N.Y.

[73] Assignee: Hi-Tek Polymers, Inc., Jeffersontown, Ky.

[21] Appl. No.: 357,985

[22] Filed: May 26, 1989

[51] Int. Cl.$^5$ .......................... A61K 7/40; A61K 7/42; A61K 7/44; A61K 7/46
[52] U.S. Cl. .................................... 424/59; 424/60; 514/847; 514/937; 514/938
[58] Field of Search .................................... 424/59, 60

[56] References Cited

U.S. PATENT DOCUMENTS

| | | | |
|---|---|---|---|
| 4,172,122 | 10/1979 | Kubik et al. | 424/59 |
| 4,683,134 | 7/1987 | Palinczar | 424/59 |

FOREIGN PATENT DOCUMENTS

| | | | |
|---|---|---|---|
| 1136842 | 12/1968 | United Kingdom | 536/3 |
| 2071495 | 9/1981 | United Kingdom | 424/70 |

Primary Examiner—Dale R. Ore
Attorney, Agent, or Firm—Herbert P. Price

[57] ABSTRACT

Dual action sunscreen compositions capable of both moisturizing the skin and protecting it from sunburn are made from a cationic guar, a cationic acrylic polymer and an ultraviolet absorbing sunscreening agent.

8 Claims, No Drawings

DUAL ACTION SUNSCREEN COMPOSITION

BACKGROUND OF THE INVENTION

The field of art to which this invention pertains is topical sun or radiation screening or tanning preparations.

Although the potentially damaging effects of sunlight on human skin have been well publicized, many people have occupations which require them to be exposed to the sun for long periods of time. Many others choose to spend their leisure time outdoors playing tennis or golf, swimming, fishing, skiing, or sunbathing. To protect human skin against erythema-causing radiation from the sun, a variety of sunscreening compositions have been developed which contain compounds which absorb ultraviolet light in the erythemal region.

Commercially available sun screen and sun block formulations provide excellent protection against severe sun burning of exposed skin for extended periods so long as they remain on exposed areas and are not washed off when contacted with water or perspiration. Unfortunately, bathing in pool water or ocean water will usually result in most conventional sun screen and sun block formulations being washed away from the skin thereby leaving exposed areas of skin.

In U.S. Pat. No. 4,781,914, sun screen compositions which are also moisturizer compositions are described. Such compositions are made in the form of a sprayable oil-in-water emulsion which when applied to the skin and rubbed in inverts to a water-in-oil creamy non-greasy film.

Water resistant sunscreen compositions which contain a water insoluble acrylate polymer are described in U.S. Pat. No. 4,172,122.

Substantive PABA (para-aminobenzoic acid) formulations which contain water soluble cellulosics are disclosed in U.S. Pat. No. 4,254,102.

Water-proof sunscreen compositions which contain ethyl hydroxyethyl cellulose polymers are described in U.S. Pat. No. 4,671,955.

In U.S. Pat. No. 4,559,225, water-proof sunscreen compositions which contain a cellulose polymer, a solvent, an ultra-violet sunscreening agent, and an emollient are disclosed.

Cosmetic manufacturers are constantly striving to improve personal skin care products, which not only offer protection from the sun, but also contribute to the smoothing and softening of the skin.

SUMMARY OF THE INVENTION

The invention is directed to sunscreen compositions which when applied to human skin provide protection against erytherma caused by ultraviolet radiation from sunlight. More particularly, this invention relates to sunscreen compositions capable of protecting the skin against erytherma over prolonged periods of time. Even more particularly, this invention pertains to sunscreen compositions which also act as moisturizing creams.

The sunscreen composition of this invention is made from a cationic guar, a cationic acrylic polymer and an ultraviolet absorbing sunscreen agent in a cosmetically and dermatological acceptable carrier. The cationic guar is hydroxy propyltrimethylammonium chloride guar having a DS of about 0.1 to about 0.2 and a viscosity as measured at 2 percent concentration in water at 25° C. and at a pH of 4–6.5 of 1000 to 2000 cps. The cationic guar is present in the composition in the amount of about 0.2 to about 2 weight percent based on the total weight of the composition. The cationic acrylic polymer is poly(methacrylamidopropyl trimethyl ammonium chloride) having a viscosity at 33 percent solids in water at a pH of 3.5–6.5 and at 25° C. of about 2000 to about 14,000 cps. The cationic acrylic polymer is present in the amount of about 0.2 to about 3.0 weight percent based on the total weight of the composition.

The ultraviolet absorbing sunscreen agent is present in the composition in the amount of about 0.1 to about 2 weight percent based on the weight of the total composition.

DESCRIPTION OF THE INVENTION

The cationic guar useful in this invention is the hydroxypropyl trimethylammonium chloride ether of guar gum having a DS of about 0.1 to about 0.2 and a viscosity as measured at 2 percent concentration in water at a pH of 4–6.5 of about 1,000 to about 2,000 cps, preferably 1,200 to about 1,800 cps. The cationic guar is made by reacting guar gum, a polygalactomannan, with 2,3-epoxypropyl trimethylammonium chloride or 3-chloro-2-hydroxypropyl trimethylammonium chloride using, basically, the process described in British Patent No. 1,136,842, which is hereby incorporated by reference.

The cationic acrylic polymer is poly(methacrylamidopropyl trimethyl ammonium chloride). This polymer is prepared by the free radical catalyzed polymerization of methacrylamidopropyl trimethyl ammonium chloride in water and has a viscosity, when measured at a solids content of 33 weight percent in water at a pH of 3.5 to 6.5 and a temperature of 25° C., of about 500 to about 14,000 cps, preferably about 8,000 to about 12,000 cps.

The ultraviolet absorbing sunscreen agent used in this invention is any compound or combination of compounds capable of absorbing ultraviolet light in the erythemal range of about 280 to about 320 nanometers and which are safe for use on human skin. Examples of such ultraviolet light absorbing compounds include p-aminobenzoates, p-dialkylaminobenzoates, salicylates, cinnamates, benzophenones, and acetophenones. Examples of specific ultraviolet light absorbing compounds include benzophenone-3, p-aminobenzoic acid, 2-ethyoxyethyl p-methoxycinnamate, diethanolamine p-methoxycinnamate, digalloyl trioleate, 2,2′-dihydroxy-4-methoxybenzophenone, ethylhexyl p-methoxycinnamate, 2-ethylhexyl salicylate and the like.

Compounds which absorb ultraviolet radiation having wavelengths above 320 nanometers can be added to prevent sunburn potentiality effects or to help protect people who are photosensitized to long ultraviolet radiation.

The composition of this invention contains about 0.2 to about 2 weight percent cationic guar, about 0.1 to about 2 weight percent cationic acrylic polymer and about 0.1 to about 2 weight percent ultraviolet absorbing sunscreen agent. Preferably the composition contains about 0.4 to about 1 weight percent cationic guar, about 0.2 to about 1 weight percent cationic polymer and about 0.2 to about 1 weight percent sunscreen agent, said weight percents being based on the total weight of the composition.

The compositions of this invention not only provide the human skin with sunburn protection but also act as skin care compositions to moisturize and condition the skin. The cationic guar provides epidermal viscoelastic effects and a topical smoothness effect resulting in a non-oily talc feeling. The cationic guar solutions have a pH buffering capacity which can be used to alter the pH of the skin. Acridine orange assay of protein denaturation shows a 68 percent reduction in protein denaturation which demonstrates the skin protection provided by the cationic guar solution.

The cationic acrylic polymer is highly substantive with the skin and provides an encapsulating effect to the skin, producing longer lasting softness and fragrance retention.

In addition to the cationic guar, the cationic acrylic polymer and the ultraviolet absorbing sunscreen agent, the compositions of this invention contain about 60 to about 85 weight percent water, preferably about 70 to about 80 weight percent, about 1 weight percent to about 10 weight percent emollients, about 0.5 to about 5 weight percent humectants, about 0.05 to about 2 weight percent preservatives and antioxidants, about 1 to about 5 weight percent surfactants, and less than 2 weight percent fragrance agents and coloring agents.

Examples of humectants useful in this invention are glycerine, propylene glycol, 1,3-butylene glycol, sorbitol, polyethylene glycol, hexylene glycol, and polyoxyethylene glyceryl ether.

Suitable emollients include petrolatum, mineral oil, lanolin alcohol, cyclomethicone, avocado oil, isopropyl palmetate, acetylated lanolin, cocoa butter, sesame oil, cetyl myristate and propylene glycol dicaprylate. The formulations preferably contain a mixture of several of these emollients or others which are approved for cosmetic use.

Suitable preservatives include methyl paraben, propyl paraben, diazodinyl urea, benzyl alcohol and phenoxyethanol.

Surfactants useful in this invention include glycerol monostearate, polyethylene glycol 150 distearate and the like.

The composition of this invention is described in detail in the following example. Percent as used in the examples is percent by weight based on the total weight of the composition.

EXAMPLE

Part A

To a suitable container containing 76.35 percent deionized water, was added 0.5 percent cationic guar (hydroxypropyltrimethylammonium chloride guar) having a DS of 0.14 and a viscosity, as measured at 2 percent concentration in water at 25° C. and a pH of 4-6.5, of 1500 cps, with medium agitation. One percent propylene glycol was added and the container contents were heated to 70° C.

Part B

In another container were added with mixing 2.5 percent glycerol monostearate, 2.5 percent mineral oil, 2 percent Parsol MCX, 1.2 percent PEG 150 distearate, 1 percent acetylated lanolin, 1 percent isopropyl palmitate, 1 percent Lanette 16, 1 percent cetyl myristate, 1 percent myristyl myristate, 0.5 percent petrolatum, 0.5 percent benzophenone-3, 0.2 percent methyl paraben and 0.1 percent propyl paraben. The container contents were heated to 70° C. and were added to Part A with medium agitation.

Part C

The acrylic polymer (polymethacrylamidopropyl trimethyl ammonium chloride) at 33 percent solids in water, 1.2 percent, was mixed with 5 percent deionized water. Part C was added to Part A and Part B.

Part D

When the temperature of the mixture of Parts A, B and C reached 50° C., 0.3 percent Trolamine 99 was added to the mixture, followed by 0.3 percent of a 50 percent aqueous solution of citric acid. When the temperature of the mixture reached 43° C., 0.75 percent of cyclomethicone and 0.1 percent of a fragrance were added.

The resulting sunscreen lotion had a pH of 6.45, and a Brookfield viscosity using a No. 4 spindle at 20 RPM, 25° C. of 5750 cps. When applied to skin, the lotion not only was effective as a sunscreen, which gave long lasting protection from sunburn, but also contributed to the smoothing and softening of the skin with a non-oily after feel.

The principles, preferred embodiments and modes of operation of the present invention have been described in the foregoing specification. The invention which is intended to be protected herein, however, is not to be construed as limited to the particular forms disclosed, since there are to be regarded as illustrating rather than restrictive. Variations and changes may be made by those skilled in the art without departing from the spirit of the invention.

What is claimed is:

1. A dual action sunscreen composition comprising:
   (A) about 0.2 to about 2 weight percent of hydroxypropyltrimethyl ammonium chloride guar having a DS of about 0.1 to about 0.2 and a viscosity of 1000–2000 cps as measured at 25° C. at 2 percent concentration in water,
   (B) about 0.1 to about 2 weight percent of poly(methacrylamidopropyl trimethyl ammonium chloride) having a viscosity at 33 percent solids in water of about 2,000 to about 14,000 cps at 25° C.; and
   (C) an ultraviolet absorbing sunscreen agent in the amount of about 0.1 to about 2 weight percent, wherein A, B and C are dispersed or dissolved in a cosmetically and dermatologically acceptable carrier which contains about 70 to about 85 weight percent water wherein said weight percents are based on the weight of the composition, wherein said composition when applied to the human skin provides sunburn protection and moisturizing effect.

2. The composition of claim 1 wherein the hydroxypropyltrimethyl ammonium chloride guar has a viscosity of about 1,200 to about 1,800 cps.

3. The composition of claim 1 wherein the poly(methacrylamidopropy trimethyl ammonium chloride) has a viscosity of about 8,000 to about 12,000 cps.

4. The composition of claim 1 wherein the sunscreen agent is capable of absorbing ultraviolet light in the range of about 280 to about 320 nanometers.

5. The composition of claim 4 wherein the sunscreen agent is selected from the group consisting of p-aminobenzoates, p-dialkylaminobenzoates, salicylates, cinnamates, benzophenones and acetophenones.

6. The composition of claim 5 wherein the sunscreen agent is benzophenone-3.

7. The composition of claim 1 wherein the hydroxypropyltrimethyl ammonium chloride guar is present in the amount of about 0.4 to about 1 weight percent, wherein the poly(methacrylamidopropyl trimethyl ammonium chloride) is present in the amount of about 0.2 to about 1 weight percent and the sunscreen agent is present in the amount of about 0.2 to about 1 weight percent.

8. The composition of claim 1 wherein the composition contains emollients, humectants, preservatives, antioxidants, surfactants, fragrance agents and coloring agents.

* * * * *